United States Patent [19]

Rudman

[11] Patent Number: 4,558,033

[45] Date of Patent: Dec. 10, 1985

[54] POTENTIATION OF THE EFFECTS OF INSULIN BY PEPTIDES

[75] Inventor: Christopher G. Rudman, Thousand Oaks, Calif.

[73] Assignee: Amgen, Thousand Oaks, Calif.

[21] Appl. No.: 501,023

[22] Filed: Jun. 6, 1983

[51] Int. Cl.[4] .................... A61K 37/26; A61K 37/00
[52] U.S. Cl. ........................................... 514/4; 514/14
[58] Field of Search ................................ 424/178, 177

[56] References Cited

U.S. PATENT DOCUMENTS

| | | | |
|---|---|---|---|
| 3,912,807 | 10/1975 | Alburn et al. | 424/178 |
| 4,107,158 | 8/1978 | Lefrancier | 424/178 |
| 4,150,121 | 4/1979 | Dietze et al. | 424/178 |

OTHER PUBLICATIONS

"Atlas of Protein Sequence and Structure", vol. 5, Supp. 2, pp. 120–121 (M. Dayhoff, ed., National Biomedical Research Foundation, 1976).

Bornstein, "In Vivo and In Vitro Actions of Synthetic Part Sequences of Human Pituitary Growth Hormone", pp. 41–49 in *Growth Hormones and Related Peptides*, A. pecile, et al., eds., Excerpta Medica, Amsterdam–Oxford (1976).

Cherrington, et al., *Am. J. Physiol.*, 242: E97–E101 (1982).

Frigeri, et al., *Biochem. Biophys. Res. Comm.*, 91: 778–782 (1979).

Frigeri, et al., Proc. 64th Ann. Meeting of the Endocrine Society, San Francisco, Jun. 1982 (Abstract 88), p. 101.

Goodman, *Metabolism*, 19: 849–855 (1970).

Lewis, et al., *J. Biol. Chem.*, 253: 2679–2685 (1975).

Lewis, et al., *Biochem. Biophys. Res. Comm.*, 92: 511–516 (1980).

Lewis et al., *Endocrine Res. Comm.*, 8: 155–164 (1981).

Stewart, et al., *Solid Phase Peptide Synthesis* (W. H. Freeman, San Francisco, 1969).

Swislocki, et al., *Endocrinology*, 76: 665–672 (1965).

Yudaev, et al., *Biochem. Biophys. Res. Comm.*, 110: 866–872 (1983).

Goodman, *Ann. N.Y. Acad. Sci.*, 148: 419–440 (1968).

*Primary Examiner*—Frederick E. Waddell
*Attorney, Agent, or Firm*—Marshall, O'Toole, Gerstein, Murray & Bicknell

[57] ABSTRACT

Disclosed are novel methods and materials for developing hypoglycemic effects in mammals, including human. A pentadecapeptide ("deletion peptide") having the sequence, $NH_2$-Glu-Glu-Ala-Tyr-Ile-Pro-Lys-Glu-Gln-Lys-Tyr-Ser-Phe-Leu-Gln-COOH, is administered to the mammal contemporaneously with exogenous insulin to generate hypoglycemic effects greater than available through administration of insulin alone. The pentadecapeptide sequence is duplicative of the sequence of amino acid residues in human growth hormone in the region spanning positions thirty-two through forty-six.

5 Claims, No Drawings

POTENTIATION OF THE EFFECTS OF INSULIN BY PEPTIDES

BACKGROUND

The present invention relates generally to the development of hypoglycemic effects in mammals, including humans and, more specifically, to novel methods and materials useful in potentiating effects of exogenous insulin on glucose metabolism through use of a synthetic pentadecapeptide which is structurally related to a region in human growth hormone.

The diabetes mellitus disease state is a chronic disorder affecting carbohydrate, fat and protein metabolism. A characteristic feature of idiopathic diabetes mellitus is a defective or deficient insulin secretory response giving rise to impaired carbohydrate (glucose) use and resulting hyperglycemia. Two major variants of the disease state exist. One variant, seen in about ten percent of all idiopathic diabetics, is referred to as insulin-dependent diabetes mellitus ("IDDM") or juvenile onset diabetes. This variant is frequently manifested for the first time in youth and is characterized by a progressive loss of insulin secretory function by beta cells of the pancreas and hence a progressive "dependence" on exogenous insulin for maintenance of carbohydrate metabolism. (This characteristic is shared by those non-idiopathic, or "secondary", diabetics whose disorders have their origins in pancreatic disease.) The second variant of idiopathic diabetes mellitus is referred to as non-insulin-dependent diabetes mellitus ("NIDDM") or adult onset diabetes and accounts for the remainder of the idiopathic diabetic population.

All diabetics, regardless of their genetic and environmental backgrounds or the age of onset of the disease, have in common an apparent lack of insulin or inadequate insulin function. Because transfer of glucose from the blood into muscle and fatty tissue is insulin dependent, diabetics lack the ability to utilize glucose adequately. Further, because glycogenolysis is ordinarily inhibited by insulin, the rate of glycogenolysis is elevated in the diabetic. Both these "derangements" from normal metabolic events lead to accumulation of glucose in the blood (hyperglycemia) to the point where renal glucose reabsorption capacity is exceeded and glycosuria occurs. The major source of energy for the diabetic thus becomes fatty acids derived from triglycerides stored in fatty tissue. In the liver, fatty acids are oxidized to ketone bodies which are circulated and used as an energy source by tissues. In the IDDM patient, and sometimes the NIDDM patient, the rate of formation of ketone bodies may exceed the rate of their utilization and ketosis along with metabolic acidosis may occur. Since tissues appear to be starving for glucose, dietary and tissue sources of protein are used in gluconeogenesis. Anabolic processes such as synthesis of glycogen, triglycerides and proteins are "sacrificed" to catabolic activities including glycogenolysis, gluconeogenesis and mobilization of fats. Thus, the diabetic state which has its origins as a "simple" insulin defect, results in widespread metabolic disturbances having long-term pathologic effects on nearly all organs and tissues of the body. Indeed, the diabetic state is one of the prime contributors to deaths caused by myocardial infarction, renal failure, cerebrovascular disease, atherosclerotic heart disease and systemic infections.

Diabetic therapy for IDDM patients and advanced NIDDM patients has consistently focused on administration of exogenous insulin derived from bovine and porcine sources. It is frequently the case that use of such heterologous species material gives rise to formation of anti-insulin antibodies which have activity-limiting effects and result in progressive requirements for larger doses in order to achieve desired hypoglycemic effects. This, combined with the generally progressive need of the IDDM patient for more exogenous insulin as beta-cell function is lost, tends to accelerate the pathologic effects of the diabetic state.

Use of the most common (and convenient) administrative route for exogenous insulin may itself exacerbate pathology resulting from insulin therapy. Subcutaneous injection of insulin gives rise to relatively high insulin levels in peripheral tissues and relatively low levels circulating through the liver, the primary site of endogenous insulin activity. High levels of insulin in peripheral tissue have been associated with blood vessel pathology (e.g., blood vessel constriction and permeability changes) and pathologic effects on associated peripheral tissues, e.g., diabetic retinopathy. The "swamping" effects of subcutaneously administered insulin on peripheral circulatory tissues eventually reduces the amount of insulin circulating to the liver—again resulting in the need for increased doses to achieve desired metabolic effects.

It will be apparent from the above that substantial long term benefits in insulin therapy for diabetics (especially IDDM patients) can be expected to attend the development of methods and materials for enhancing the hypoglycemic effects of exogenous insulin. If insulin therapy for a given patient is expected to continue over a period of decades, it is significant that initial doses be as small as possible and that large doses of exogenous insulin be avoided for as long as possible.

The recent past has seen modest advances in the development of chemical agents capable of stimulating endogenous insulin secretion and hence reducing the need for exogenous insulin in large doses. Further, recombinant DNA methods have been brought to bear on the problem of securing large scale production of homologous species (human) insulin with the hope that use of the "human" material will reduce the progressive need for larger doses of insulin resulting from the effects of anti-insulin antibodies made against heterologous species materials. As yet, however, no significant advances have been reported in research directed toward development of compounds which would function to augment hypoglycemic effects of any given dose of endogenous insulin and thus guarantee that the insulin dose regimen employed can always be set at or near the minimum needed for desired metabolic effect and will result in the minimum of adverse side effects. There continues to exist, therefore, a need in the art for methods and materials for enhancing the hypoglycemic effects of exogenous insulin in mammals, including humans.

Of interest to the background of the invention are the results of certain studies on insulin-like activities of human growth hormone ("hGH"). hGH is a relatively high molecular weight polypeptide (~22,000 Daltons) consisting of a continuous sequence of 191 amino acid residues with secondary structure provided by two disulfide bonds formed between cysteine residues at position numbers 53/165 and 182/189, respectively. ["Atlas of Protein Sequence and Structure," Vol.5, Supp.2, pp.120-121 (M. Dayhoff, ed., National Biomedical Research Foundation, 1976)]. Early studies of the growth promoting effects of hGH revealed, as one of its intrinsic properties, the ability to initially raise and then lower blood levels of glucose and to lower free fatty acids within one hour of administration, followed by later increasing circulating fatty acids. See, e.g., Goodman, *Metabolism*, 19, pp. 849–855 (1970); Goodman, *Ann. N.Y. Acad. Sci.*, 148, pp. 419–440 (1968); and Swislocki, et al. *Endocrinology*, 76, pp. 665–672 (1965). The hyperglycemic and hypoglycemic effects of large doses of hGH are so pronounced in many cases that they constitute a substantial adverse side-effect of hGH therapy for growth disorders.

Determination of the effects of hGH on glycemia prompted a series of studies into the in vivo and in vitro actions of peptide fragments and synthetic fragments related to amino and carboxy terminal regions of hGH. See, e.g., the review by Bornstein appearing at pp.41–49 in "Growth Hormones and Related Peptides," A. Pecile, et al., eds. Excerpta Medica, Amsterdam-Oxford (1976). A variety of biological effects were noted including an insulin potentiating effect on glucose uptake by a fragment duplicating the sequence of amino acid residues at hGH positions 1 through 15 and a hyperglycemic effect for a peptide duplicating residues 176 through 191.

The discovery by Lewis, et al. in 1975 [*J.Biol.Chem.*, 253, pp. 2679–2685] of a naturally-occurring structural variant of hGH which differed from the major form of the hormone by having fewer amino acid residues prompted a systematic examination of the variant, 20,000 Dalton polypeptide, and its properties. Studies by Frigeri, et al., *Biochem. Biophys. Res. Comm.*, 91, pp. 778–782 (1979), Lewis, et al., *Biochem. Biophys. Res. Comm.*, 92, pp. 511–516 (1980), and Lewis, et al., *Endocrine Res. Comm.*, 8, pp. 155–164 (1981) established that the 20,000 Dalton variant lacked the hypoglycemic and fatty acid lowering effects of hGH but substantially retained its growth promotant effects. It was also determined that the "missing" amino acid residues were in a region spanning positions thirty-two to forty-six of hGH. Following these publications were reports of further studies directed toward ascertaining the role of the "missing" residues in the growth stimulating and insulin-like activities of hGH. Frigeri, et al., [Proc. 64th Ann. Meeting of the Endocrine Society, San Francisco, June 1982 (Abstract 88), p. 101]reported that, in normal rats, a synthetic peptide corresponding to residues 32 to 46 of hGH did not show either the late increases in free fatty acids nor the glycemic effects which are characteristic of intact hGH. An unspecified degree of improvement in glucose tolerance of a GT-impaired strain of mice (YS/Wf Nctr) was observed for the peptide, as was an in vitro increase in glucose utilization of insulin-stimulated fat cells of older obese rats. Yudaev, et al., *Biochem. Biophys. Res. Comm.*, 110, pp. 866–872 (1983) reported substantially the same in vitro effects on fat cells for a synthetic tetradecapeptide having a sequence of amino acids copying residues at positions 31 through 44, and reiterated an earlier report of the absence of any in vivo hypoglycemic effect for the tetradecapeptide in rabbits and normal rats. In sum, the above-noted studies revealed that while hGH displays substantial glycemic effects in vivo which are not shown by the 20,000 Dalton variant, the "missing" sequence had no glycemic effect in vivo unless provided to the test animal as part of the hGH polypeptide.

BRIEF SUMMARY

In one of its aspects, the present invention provides improvements in insulin therapy methods for securing the reduction of circulating glucose in mammals, including humans, which involve periodic parenteral administration of exogenous insulin. The improved methods comprise augmenting the physiological effectiveness of insulin as a hypoglycemic agent by means of contemporaneous (e.g., simultaneous) administration of an effective amount of a synthetic pentadecapeptide having the structure, $NH_2$-Glu-Glu-Ala-Tyr-Ile-Pro-Lys-Glu-Gln-Lys-Tyr-Ser-Phe-Leu-Gln-COOH. The pentadecapeptide sequence is duplicative of the sequence of amino acid residues in human growth hormone in the region spanning positions thirty-two through forty-six.

In a presently preferred form, the improved therapeutic methods of the invention are accomplished by administration of novel pharmaceutical compositions comprising effective amounts of insulin and the pentadecapeptide (referred to as "deletion peptide", "DP", or $hGH_{32-46}$) combined with a pharmaceutically acceptable diluent, adjuvant or carrier. Such compositions, suitable for effecting the contemporaneous (e.g., simultaneous) parenteral (e.g., subcutaneous) administration of active agents may include insulin and deletion peptide in relative ratios ranging from about 1 mU insulin to 100 mg DP to about 100 mU insulin to 1 $\mu$g DP and preferably about 1 mU insulin to 1 $\mu$g DP.

In another of its aspects, the present invention is seen to comprise a novel process for the formulation of (homologous or heterologous species) exogenous insulin-containing compositions for use in controlling the levels of circulating glucose in mammals wherein a selected desired hypoglycemic effect is determined to require the use of a predetermined quantity of insulin. According to the improved process, less than the predetermined quantity of insulin is incorporated but there is incorporated for contemporaneous administration an effective quantity of deletion peptide.

Other aspects and advantages of the present invention will be apparent upon consideration of the following detailed description of the invention including illustrative examples of the practice thereof. As employed therein and in the claims, the terms, "$hGH_{32-46}$", "deletion peptide", and "DP" shall be used synonymously to designate a peptide of the sequence: $NH_2$-Glu-Glu-Ala-Tyr-Ile-Pro-Lys-Glu-Gln-Lys-Tyr-Ser-Phe-Leu-Gln-COOH.

DETAILED DESCRIPTION

The present invention has its origins, in part, in the results of an extensive series of controlled experiments designed to study the effects of deletion peptide: (a) on in vivo glucose metabolism in normal rats; (b) on in vivo insulin-stimulated glucose uptake by normal rat liver and skeletal muscle tissue; (c) on growth of hypophysectomized rats; and (d) on in vitro glucose utilization of adipocytes isolated from normal rats. Briefly put, these studies revealed that deletion peptide had small, insulin-like effects in increasing hepatic glycogen synthesis when administered alone and that administration in combination with insulin caused an alteration in the incorporation of labelled glucose into liver and skeletal muscle tissue. The studies showed no growth stimulating effect for deletion peptide on hypophysectomized rats and no effect on insulin-stimulated glucose uptake by isolated adipocytes. This last observation was inconsistent with the findings of Frigeri, et al. (1982, supra) and Yudaev, et al. (1983, supra), but the studies did substantiate the findings of the two publications to the extent that it was found that deletion peptide had no hypoglycemic effect on normal rats. What the studies unexpectedly revealed was that, despite lack of hypoglycemic efects (and thus the lack of endogenous insulin potentiating effects) when deletion peptide was administered alone, the synthetic peptide substantially augmented the effects of exogenous insulin when concurrently administered therewith.

The remarkable results noted in these experiments gave rise to another extensive series of studies which were specifically directed to determining insulin potentiating effects of deletion peptide on various animal models including rats, normal and genetically abnormal mice, dogs and, finally, primates. The following illustrative examples of practice of the invention are therefore directed to: (1) synthesis of deletion peptide; (2) determination of deletion peptide effects on glycemia in rats in the presence and absence of exogenous insulin; (3) determination of the effect of varying levels of exogenous insulin dose on glycemia in rats in the presence and absence of deletion peptide; (4) the effects of deletion peptide on hypoglycemic activity of fixed exogenous insulin doses in normal rats, normal mice, and genetically altered mice; (5) the effects of deletion peptide on glycemia in normal dogs or dogs treated to suppress endogenous insulin secretion and then treated with exogenous insulin; and (6) the effects of deletion peptide on hypoglycemic activity of fixed doses of exogenous insulin supplied to monkeys.

EXAMPLE 1

A synthetic pentadecapeptide having the amino acid sequence, $NH_2$-Glu-Glu-Ala-Tyr-Ile-Pro-Lys-Glu-Gln-Lys-Tyr-Ser-Phe-Leu-Gln-COOH, is suitably manufactured according to the general method of Stewart, et al., *Solid Phase Peptide Synthesis* (W.H. Freeman, San Francisco, 1969). Briefly put, the peptide is constructed by means of a series of amino acid residue additions to an initial, column-bound, glutamine residue providing the carboxy terminal residue of the resultant pentadecapeptide. Deletion peptide is obtained as a white lyophilized powder which migrates as a single spot on thin layer chromatography.

EXAMPLE 2

A study was conducted to determine the effect on plasma glucose of deletion peptide, with and without insulin, in rats given an intraperitoneal glucose load. Groups of five male Sprague-Dawley rats were involved in this study. All weighed between 160 to 168 grams and were maintained on standard laboratory diet until 18 hours prior to the test procedures. Test groups of fasted rats received, in rapid succession, 1.0 ml of 0.75 M glucose, 10 mU of insulin in admixture with 1% bovine serum albumin (BSA) in normal saline (pH 7.4), and either 0, 25, 50 or 100 µg doses of deletion peptide. Control groups of rats received glucose and 1% BSA in saline with no insulin but with similarly varying levels of deletion peptide. Plasma glucose determinations were made on blood drawn one hour after administration of test substances and the results (means, ± standard errors) of these determinations are set out in Table I below.

TABLE I

| | Plasma Glucose (mmol/l, at 60 minutes) | | |
|---|---|---|---|
| Dose of DP per Rat, in µg | 1.0% BSA in Saline | 10 mU Insulin in 1.0% BSA in Saline | P. Value |
| 0 | 7.9 ± 1.0 | 8.1 ± 0.2 | NS |
| 25 | 8.1 ± 0.2 | 7.5 ± 0.1 | <0.5 |
| 50 | 7.7 ± 0.2 | 5.7 ± 0.3 | <0.01 |
| 100 | 8.0 ± 0.4 | 3.5 ± 0.1 | <0.001 |

As indicated in Table I, administration of deletion peptide in amounts up to 100 µg/rat was without effect on glycemia. The lowest dose of deletion peptide, however, produced a small significant decrease in plasma glucose when given with a low dose of insulin in BSA which itself was without effect on glycemia (compare "0" dose DP values for BSA and BSA plus insulin). Increasing doses of deletion peptide resulted in progressively greater degrees of hypoglycemic effects.

EXAMPLE 3

A study was conducted under the same general procedures as Example 2 to determine the effect of increasing doses of insulin, with and without 100 µg of deletion peptide, on rats given an intraperitoneal glucose load. The results of plasma glucose determinations on blood drawn after 60 minutes are set out below in Table II.

TABLE II

| | Plasma Glucose (mmol/l, at 60 minutes) | | |
|---|---|---|---|
| Dose of Insulin per Rat, in mU | 1.0% BSA in Saline | 100 µg DP in 1.0% BSA in Saline | P. Value |
| 0 | 7.0 ± 0.1 | 8.1 ± 0.2 | NS |
| 7 | 8.0 ± 0.3 | 7.6 ± 0.1 | NS |
| 10 | 8.1 ± 0.2 | 3.5 ± 0.1 | <0.001 |
| 20 | 7.0 ± 0.1 | 3.1 ± 0.1 | <0.001 |
| 40 | 5.2 ± 0.3 | 2.7 ± 0.1 | <0.001 |

As indicated in Table II, the lowest dose of insulin tested, 7.0 mU/rat, caused no change in glycemia compared with the control group, whether or not deletion peptide was concurrently administered. When animals received deletion peptide in addition to 10 mU insulin there was a significant degree of hypoglycemia even though insulin alone at this dose was without effect on plasma glucose concentration. Higher doses of insulin produced corresponding decreases in plasma glucose and these hypoglycemic effects were potentiated by the presence of deletion peptide.

The data set out in Table II serve to illustrate that aspect of the invention which relates to improved formulating processes in insulin therapy for the control of circulating glucose. As indicated in the Table, when it is desired to secure a reduction in plasma glucose for the glucosestressed animal from about 8.0 mmol/1 to about 5.2 mmol/1, attainment of this specified desired effect can be achieved by incorporation of a predetermined dose of 40 mU of exogenous insulin in the pharmaceutical composition administered. According to the invention, the same or even greater hypoglycemic effects can be attained by incorporating only 10 mU of exogenous insulin in the composition administered, if such administration is accompanied by incorporation for contemporaneous administration of an effective amount (about 100 µg) of deletion peptide.

EXAMPLE 4

A study was conducted to ascertain the effects of fixed amounts of deletion peptide and insulin on various animal models, including rats and normal and genetically abnormal mice.

Animals in test groups of five each were employed in these procedures. Sprague-Dawley rats weighed approximately 200 grams; homozygous genetically abnormal mice (ob/ob and db/db) had weights in the range of 40 to 60 grams; and heterozygous normal mice (ob/+ and db/m) all weighed approximately 25 grams. Glucose was administered intraperitoneally at a dosage of 0.05 ml/10g of a solution containing 135 mg/ml glucose, except for one group of rats which were given an oral dose of glucose comprising 1 ml of 270 mg/ml glucose solution. Insulin was administered at a dose of 0.001 mU/10g and deletion peptide was simultaneously intraperitoneally administered at a dose of 5.0 µg/10g.

The results of plasma glucose determinations performed on blood drawn one hour after administration of test materials are set out in Table III, below. In all animals tested, deletion peptide potentiated the hypoglycemic activity of insulin.

TABLE III

| Animal Model | Plasma Glucose (mg/ml at 60 min) | | |
| --- | --- | --- | --- |
| | Glucose | Glucose + Insulin | Glucose + Insulin + DP |
| Mouse ob/ob | 222.0 ± 35 | 167.4 ± 26 | 138.2 ± 11 |
| Mouse ob/+ (normal) | 120.0 ± 12 | 99.5 ± 6 | 56.0 ± 9 |
| Mouse db/db | 320.0 ± 75 | 198.2 ± 31 | 134.0 ± 13 |
| Mouse db/m (normal) | 99.0 ± 9 | 102.0 ± 10 | 49.0 ± 12 |
| Rat (normal) | 150.0 ± 11 | 121.0 ± 28 | 73.0 ± 10 |
| Rat* (normal) | 184.0 ± 14 | 144.0 ± 12 | 93.3 ± 14 |

*Glucose administered orally

EXAMPLE 5

Two studies were conducted to determine the effects of deletion peptide on dogs. In the first study, a normal dog was used which had been prepared (per the procedures of Cherrington, et al, Am.J.Physiol., 242, pp. E97–E101 (1982), with silastic catheter implants in the femoral artery and the portal, hepatic and splenic veins to allow for determination of glycemic effects throughout major circulatory vessels of the body. Deletion peptide was infused into the dog at the portal catheter at a rate of 1 µg/kg/min, giving rise to plasma levels of about 40 ng/ml. Apart from a minor transient fall in plasma and hepatic glucose output, deletion peptide administration produced no glycemic effects over a period of two hours. There was a transient increase in insulin levels of from 11 to 15 mU per ml in peripheral blood.

In the second study, deletion peptide was infused portally at a rate of 1 µg/kg/min during hyperglycemia induced by infusing glucose through a peripheral catheter (to maintain glucose levels in excess of 200 mg/deciliter). Basal glucagon levels were fixed and insulin levels were fixed either at basal or four-fold basal levels. The results were somewhat variable but indicated that basal level exogenous insulin with deletion peptide caused hepatic glucose uptake, unlike basal insulin alone which only reduced hepatic glucose output. When insulin levels were increased four-fold, however, the degree of hepatic glucose uptake increased sharply.

EXAMPLE 6

A study was conducted to determine the effects of deletion peptide on induced hyperglycemia in Rhesus monkeys. Blood samples were taken from normal female monkeys (in three experimental groups of three) five minutes before administration of an oral dose of 3.0 ml/kg of 0.5 g/ml glucose and intramuscular administration of either: (1) 0.5 ml/kg phosphate buffered saline (PBS), pH 7.4; (2) deletion peptide 0.1 ml/kg of 1.0 mg/ml solution in PBS; (3) deletion peptide as above combined with 0.5 ml/kg of 20 mU/ml insulin in PBS; or (4) insulin alone as above. Blood samples were then periodically withdrawn over two hours and analyzed for plasma glucose levels. Plasma glucose level data is set out in Table IV. At all post-injection times, deletion peptide potentiated insulin effects.

TABLE IV

| Time | Plasma Glucose (mg/ml) | | |
| --- | --- | --- | --- |
| | Glucose Alone | Glucose + Insulin | Glucose + Insulin + DP |
| −5 min. | 84.6 ± 7.5 | 71.0 ± 3.0 | 70.0 ± 2.5 |
| +5 min. | 82.5 ± 6.2 | 79.0 ± 9.0 | 64.0 ± 4.0 |
| +15 min. | 106.0 ± 14 | 72.0 ± 10 | 69.0 ± 9.0 |
| +30 min. | 117.0 ± 16 | 85.0 ± 11 | 80.0 ± 5.3 |
| +45 min. | 132.0 ± 13 | 88.0 ± 13 | 80.0 ± 5.9 |
| +60 min. | 125.0 ± 12 | 109.0 ± 14 | 96.0 ± 8.0 |
| +120 min. | 126.0 ± 12 | 108.0 ± 14 | 97.0 ± 6.6 |

The foregoing illustrative examples are believed to establish with certainty that the hypoglycemic effects of exogenous insulin are substantially enhanced or potentiated when accompanied by contemporaneous administration with deletion peptide. While practice of the methods of the invention may comprehend contemporaneous parenteral administration of deletion peptide prior to or subsequent to insulin administration, it is expected that the most highly augmentative effects will be observed by simultaneous administration of both materials. In this regard, it is expected the significant beneficial effects will attend parenteral (e.g., subcutaneous administration of pharmaceutical compositions of the invention comprising admixtures of insulin and deletion peptide along with pharmaceutically acceptable diluents, adjuvants and carriers such as are commonly employed in administration of insulin alone. Suitable compositions are expected to result from use of admixtures of insulin and deletion peptide in relative weight ratios varying from 1 mU insulin to 100 µg DP to about 100 mU insulin to 1 µg DP with a preferred ratio, based on the procedures of the above examples, of about 1mU to 1 µDP.

The above examples establish that deletion peptide alone has no immediate and direct hypoglyamic effect within the protocols of investigations conducted to date. Ongoing studies of deletion peptide biological activities in in vivo systems have revealed preliminary evidence of insulin secretory stimulation effects, effects on levels of free fatty acids, and effects on glucose uptake by hepatic and muscle tissue. Further, certain of these effects appear to be shared by peptides disclosed and claimed in co-owned, co-pending, concurrently-filed U.S. Patent application Ser. No. 501,024, by the inventor herein and co-inventor Theodore Jones, entitled "Biologically Active Peptides Structurally Related to Regions Within Growth Hormones," the disclosures of which are incorporated by reference herein.

While solid phase synthesis according to the procedures of Example 1 constitutes the presently preferred method for securing production of deletion peptide in quantity, use of alternative methods such as liquid phase synthesis, microbial synthesis by recombinant DNA techniques and isolation of deletion peptide as a fraction from naturally-occurring hGH is contemplated.

Numerous modifications and variations in practice of the present invention are expected to occur to those skilled in the art upon consideration of the foregoing detailed description of illustrative embodiments thereof and therefore only such limitations should be placed on the scope of the invention as appear in the appended claims.

What is claimed is:

1. In the method for securing reduction of circulating glucose in mammals by administering exogenous insulin to the mammal, the improvement comprising augmenting the physiological effectiveness of insulin administered by contemporaneously administering an effective amount of deletion peptide.

2. The improved method of claim 1 wherein insulin and deletion peptide are administered simultaneously.

3. The improved method of claim 1 wherein insulin and deletion peptide are administered subcutaneously.

4. A pharmaceutical composition for use in reducing levels of circulating glucose in mammals, said composition comprising the admixture of insulin and deletion peptide together with a pharmaceutically acceptable diluent, adjuvant or carrier.

5. A composition according to claim 4 comprising the admixture of insulin and deletion peptide in a relative weight ratio of from about 1 mU insulin to 100 $\mu$g deletion peptide to about 100 mU insulin to 1 $\mu$g deletion peptide.

* * * * *

UNITED STATES PATENT AND TRADEMARK OFFICE
CERTIFICATE OF CORRECTION

PATENT NO. : 4,558,033

DATED : December 10, 1985

INVENTOR(S) : CHRISTOPHER G. RUDMAN

It is certified that error appears in the above-identified patent and that said Letters Patent is hereby corrected as shown below:

Column 6, line 7, change "7.9 $\pm$ 1.0" to --7.9 $\pm$ 0.1--.

Signed and Sealed this

Eighteenth Day of November, 1986

Attest:

DONALD J. QUIGG

*Attesting Officer*  *Commissioner of Patents and Trademarks*